United States Patent [19]
Diaz et al.

[11] Patent Number: 5,370,129
[45] Date of Patent: Dec. 6, 1994

[54] IUD INSERTING APPARATUS

[75] Inventors: Juan Diaz, Sao Paulo, Brazil; Lance J. Bronnenkant, Snyder, N.Y.

[73] Assignee: DB Inserters, Inc., North Tonawanda, N.Y.

[21] Appl. No.: 938,208

[22] Filed: Aug. 28, 1992

[51] Int. Cl.$^5$ ............................ A61F 6/14; A61F 6/06
[52] U.S. Cl. .................................. 128/839; 128/840
[58] Field of Search ................................ 128/830–841

[56] References Cited

U.S. PATENT DOCUMENTS

| | | | |
|---|---|---|---|
| 3,842,826 | 10/1974 | Nolan | 128/840 |
| 3,880,156 | 4/1975 | Hoff | 128/840 |
| 3,918,444 | 11/1975 | Hoff | 128/840 |
| 3,927,666 | 12/1975 | Hoff | 128/840 |
| 4,019,633 | 4/1977 | Roth . | |
| 4,026,281 | 5/1977 | Mayberry | 128/840 |
| 4,143,656 | 3/1979 | Holmes | 128/840 |
| 4,249,525 | 2/1981 | Krzeminski | 128/840 |
| 4,561,433 | 12/1985 | Wheeler | 128/840 |
| 4,678,463 | 7/1987 | Millar | 128/840 |

*Primary Examiner*—Michael A. Brown
*Attorney, Agent, or Firm*—Lerner, David, Littenberg, Krumholz & Mentlik

[57] ABSTRACT

Methods and apparatus are disclosed for permitting a user to load an IUD into an IUD inserter within the confines of a tray and thereafter to safely insert the IUD into a patient's uterus to the proper depth while minimizing the risk of causing trauma to the uterine wall. An IUD inserter comprises an elongate shaft adapted to retain the arms of an IUD adjacent the distal end of the shaft, a slidable arm retainer mounted on the shaft adaptable to abut the outer portion of a patient's cervix, and a stop member adjustably mounted on the shaft so that the arm retainer is forced by the outer portion of a patient's cervix to abut the stop member as the IUD is advanced through the cervical canal of a patient to a preselected depth at the uterine fundus. An associated package permits an IUD having expandable arms thereon to be loaded into an arm retainer within the confines of the package immediately prior to insertion of the IUD into a patient's uterus. When it is desirable to insert the IUD into a patient after loading same in the arm retainer of an inserter, the steps include placing the slidable arm retainer of an IUD inserter against the outer portion of a patient's cervix, aligning the inserter and the IUD device therein with the cervical opening.

17 Claims, 6 Drawing Sheets

IUD INSERTING APPARATUS

FIELD OF THE INVENTION

The present invention relates to an intrauterine device ("IUD") inserter apparatus, to a tray for storing and "loading" an IUD into a portion of IUD inserter, and to methods of handling and inserting IUDs.

BACKGROUND OF THE INVENTION

The prior art is replete with IUDs and IUD inserters for placing an IUD into a uterus of a patient. In the past, many attempts have been made to safely assure that the IUD will be placed at the proper depth at the uterine fundus. However, the prior art methods and apparatus for inserting an IUD have been inadequate in their attempts to achieve a satisfactory degree of safety while inserting the IUD. In one known prior art IUD inserter, formerly used by the applicant, the IUD inserter comprised a tubular cannula in which the IUD is stored, a flange connected to a portion of the cannula to indicate the proper depth of a patient's uterus and an elongate plunger sized and shaped to be inserted within the cannula. While the cannula containing the IUD is inserted into a patient's uterus to the uterine fundus, the IUD is forced from the cannula by the distal end of the associated plunger. This prior art IUD inserter depends solely on the skill of the operator for proper placement.

U.S. Pat. No. 3,918,444 to Hoff et al. is directed toward an IUD inserter apparatus comprising an elongate tube and a slidable cap having slots disposed therein to receive corresponding arm members of an associated IUD. The function of the cap is to restrain the arm members and to facilitate insertion of the IUD. The IUD inserter disclosed in the '444 patent likewise depends on the skill of the operator to achieve proper IUD placement and to avoid trauma to the uterine wall.

U.S. Pat. No. 3,927,666 to Hoff discloses an IUD inserter comprising an elongate tube having a small diameter section and a large diameter section for retaining an IUD therein. A collar is arranged around the circumference of the larger diameter section of the inserter tube. The collar abuts the cervix to arrest motion of the tube. Such a collar tends to reduce the likelihood of injury to the wall of a patient's uterus. The inserter of the '666 patent has obvious drawbacks in that the expandable arms of an associated T-shaped IUD must be aligned with the entrance of a patient's cervix for insertion into the uterus without the aid of an arm retainer or any guide means whatsoever.

Furthermore, packaging trays for IUDs and IUD inserters, as well as packaging for other medical instruments, are well-known in the art. With respect to trays for an IUD inserting apparatus, U.S. Pat. No. 4,019,633 to Roth discloses a package for an IUD and an IUD inserter comprising a thermoformed plastic tray having a cavity therein for holding an IUD and an IUD inserter, a cover therefor, and an adhesive coating for attaching the aforementioned cover to the plastic tray. As shown in FIG. 2 of the '633 patent, a cavity permits the arms of an IUD to remain in an expanded T-shaped position within a cap of an associated IUD inserter device. However, the foregoing tray is defective in that the IUD and its associated inserter must be removed from the sterilized environment of the tray prior to "loading" the arms of the IUD into cap of the IUD inserter so that the arms can be held in a substantially folded position.

Another IUD, IUD inserter and tray therefor manufactured by the German company Nourypharma GmbH and sold under the trade name MULTILOAD CU250. This device includes a tube-type inserter having a collar thereon such that the collar can directly abut the cervix upon insertion. A tray includes four separate compartments for retaining the collar. Additionally, the tray includes a scale consisting of the numerical indicia 6, 7, 8 and 9 cm arranged adjacent a respective compartment for retaining the collar. These compartments serve the purpose of retaining the collar and aligning it with a depth in centimeters corresponding to a uterus sounding measurement of a particular patient. The MULTILOAD CU250 tray includes several shortcomings which hamper the effectiveness and usefulness of the tray disclosed therein. In particular, the MULTILOAD CU250 tray does not include means for "loading" expandable arms of an IUD into an inserter immediately before inserting the IUD into the uterus of a patient. Additionally, the separate compartments for retaining the collar inhibit the precise setting of the collar to the proper depth for an individual patient. Furthermore, the MULTILOAD CU250 tray does not prevent the arms of an IUD from spinning or twisting prior to insertion or during insertion of the IUD into the cervical os. Thus, the arms of the IUD may not be properly aligned when the IUD is placed into the uterus of a patient.

Thus, despite all of the efforts in the prior art, improved methods and apparatus for inserting an IUD into the uterus of a patient are needed.

SUMMARY OF THE INVENTION

The present invention addresses the aforementioned shortcomings of the prior art.

One aspect of the present invention provides an apparatus for safely inserting an IUD without the risk of causing an injury to the uterine wall of a patient. The apparatus according to this aspect of the present invention includes an elongate shaft having a proximal end and a distal end, wherein the shaft is adapted to retain the IUD adjacent the distal end. A first member having a leading end and a trailing end is slidably mounted on the elongate shaft and is adapted so that the leading end abuts the outer portion of a patient's cervix during insertion of the IUD into the uterus. A depth stop member is adjustably mounted on the elongate shaft and is arranged to abut the trailing end of the leading member when the distal end of the elongate shaft is advanced through the cervical canal of a patient to a preselected depth at the uterine fundus while the leading end of the first member remains in abutment with the outer portion of the cervix. Thus, a doctor or other qualified individual will insert the IUD to the proper depth at the uterine fundus of a patient without the risk of causing trauma to the wall of the patient's uterus.

In a particularly preferred arrangement, the first member of the IUD inserter is an arm retainer comprising a body. The body of the arm retainer is hollow so as to define a passageway therethrough from the trailing end to the leading end. The elongate shaft may comprise a hollow tube in which a part of the IUD is retained during insertion of same. In a particularly preferred arrangement, the widthwise dimension of the passageway through the arm retainer is narrower at the leading end than it is at the trailing end. Thus, the expandable arms on the IUD are gradually folded as the IUD and inserter tube are advanced distally into the passageway through the trailing end of the arm retainer and toward the leading end thereof. The arm retainer desirably includes a collar formed about the leading end. The collar is arranged to abut the outer portion of a patient's cervix during insertion of the IUD into the uterus.

Another aspect of the present invention provides a tray for retaining an IUD having expandable arms thereon and an IUD inserter. The tray according to this aspect of the present invention includes means for retaining an elongate shaft of an IUD inserter having an IUD thereon so that the arms of the IUD are arranged in the tray in an expanded position. The elongate shaft includes a proximal end and a distal end and is disposed in the tray so that the expanded arms are arranged adjacent the distal end of the elongate shaft. The tray according to this aspect of the present invention most preferably also comprises means for retaining an arm retainer of the inserter having a leading end and a trailing end so that the trailing end lies adjacent the expanded arms. Thus, the arms of the IUD will become folded as the elongate shaft is advanced distally into the trailing end of the arm retainer while the elongate shaft and the arm retainer remain in the tray.

In a particularly preferred arrangement of this aspect of the present invention, the tray also includes means for retaining a depth stop member, such as a flange, so that the flange can be continuously adjusted along the shaft to correspond with a predetermined uterine depth indicating the distance between the outer portion of a patient's cervix and the uterine fundus. It is also desirable for the tray to include measurement indicia thereon. Most preferably, the indicia represents a preselected range of uterine depths and is disposed adjacent the means for retaining a flange so that the flange can be adjusted to a location adjacent the appropriate indicia which represents the depth of a particular patient's uterus. It is also preferable for the flange compartment of the tray to include means for preventing the flange from being adjusted to a uterine depth of less than the recommended depth for the particular type of IUD therein. This means serves as an additional safeguard to prevent the IUD from being inserted beyond a preselected depth defined by a patient's uterine fundus, and therefore, may prevent trauma from occurring thereat. Additionally, it is preferable for the tray of the present invention to include means for receiving at least a portion of the arms of the IUD when the arms are arranged in a substantially folded position and at least partially extend out of the leading end of the arm retainer.

Most preferably, a tray according to this aspect of the present invention comprises a housing having a distal end and a proximal end. The housing should include a cavity for receiving the IUD inserter having an IUD therein. It is desirable for the cavity to be continuous and to include an elongate shaft compartment for retaining the elongate shaft of the IUD inserter. Further, the cavity should include an expandable arm compartment connected to the elongate shaft compartment at the distal end thereof for retaining the arms of the IUD in their expanded position. It is also preferable for the cavity of the tray to include an arm retainer compartment adjacent the expandable arm compartment toward the distal end of the housing. The arm retainer compartment may be arranged to receive an arm retainer having a trailing end and a leading end and a passageway therethrough so that the expandable arms can be advanced through the trailing end of the passageway toward the leading end of the arm retainer at the distal end of the housing.

The tray may have a flange compartment connected to the elongate shaft compartment proximal to the expandable arm compartment for receiving a flange therein. The flange compartment desirably is continuous for precise adjustment of the flange. As can be appreciated, a tray according to this aspect of the present invention can be used for "loading" the expandable arms of an IUD in their folded position in an arm retainer immediately prior to insertion into the uterus of a patient while the IUD and its associated inserter remain within the confines of the tray.

Another aspect of the present invention provides a method for loading expandable arms of an IUD into an arm retainer of an IUD inserter while the IUD and the inserter remain in a tray, such as a tray according to the aforementioned preferred embodiments. The arms of the IUD desirably are permitted to remain in their expanded T-shaped state until immediately prior to insertion of the IUD into a patient. A method according to this aspect of the present invention includes the step of advancing the distal end of the elongate shaft of the inserter into an arm retainer as discussed above so that the arms of the IUD are forced from their expanded position to a substantially folded position therein. This advancing movement desirably terminates when the IUD abuts a portion of the tray adjacent the leading end of the arm retainer.

The preferred methods for loading the expandable arms of an IUD in an arm retainer of an inserter in accordance with this aspect of the present invention effectively permits a doctor or other qualified individual to "load" the normally expanded arms of an IUD into their folded position within an arm retainer immediately prior to insertion of the IUD into a patient. Additionally, this preferred method permits a user to precisely adjust the stop member to an exact depth of a particular patient's uterine fundus to assure that the IUD will be inserted to the proper depth without injury to the uterine wall. The loading and adjusting operations can be performed within the aseptic environment of the tray in which the IUD and its associated inserter were originally packaged.

Still another aspect of the present invention provides a method for safely inserting an IUD to the proper depth within a patient's uterus while minimizing the risk of damaging the uterine wall. A method according to this aspect of the present invention includes the steps of placing a slidable member, such as an arm retainer, of an IUD inserter against the outer portion of a patient's cervix, wherein the inserter includes an elongate shaft preferably in the form of an elongate tube having distal and proximal ends thereon and an IUD on the distal end. The inserter is then aligned with the cervical opening while the slidable member is maintained in abutment with the outer portion of the cervix. The distal end of the inserter is then advanced through the cervical canal and into the uterus. In this step, the proximal end of the elongate shaft is advanced toward the slidable member until the slidable member abuts a stop member, such as a flange, which is arranged at a predetermined location on the elongate shaft. The elongate shaft of the inserter is then withdrawn from the uterus and out of the cervical opening while the IUD, with its arms fully expanded at the uterine fundus, is left at the proper location within the patient.

These and other objects of the present invention will be more clearly understood when read in conjunction with the detailed description and the accompanying drawings which follow.

DESCRIPTION OF THE DETAILED EMBODIMENTS

Figure 1:
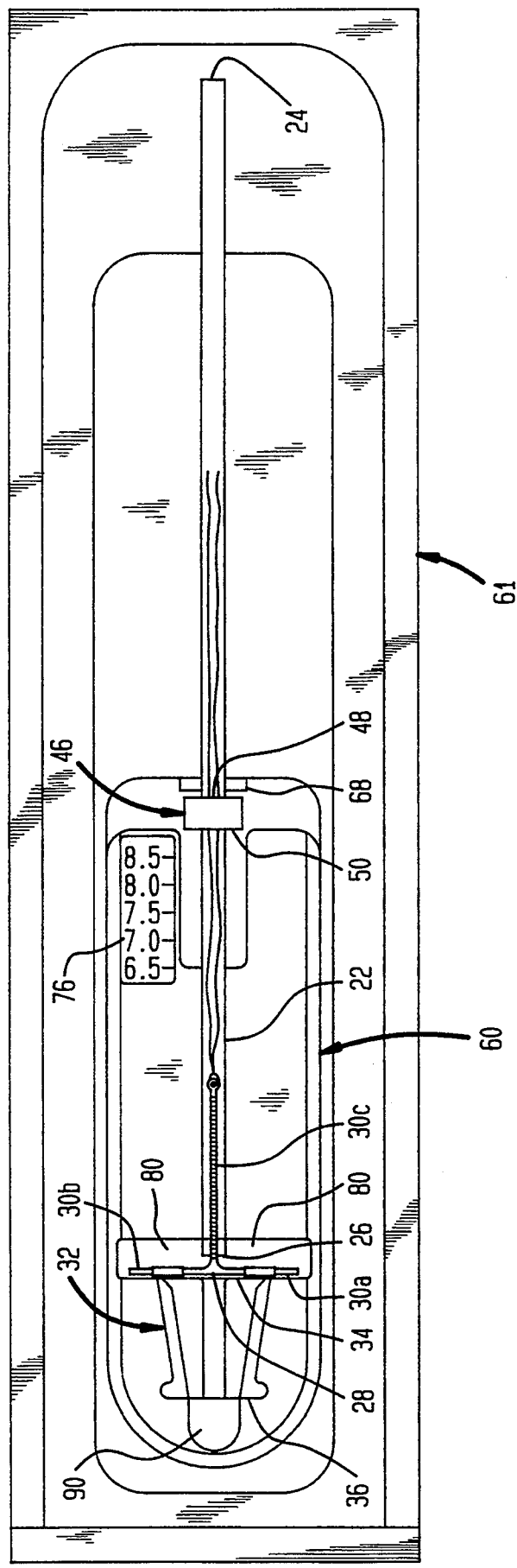
FIG. 1 is a diagrammatic plan view depicting one embodiment of the present invention.

An IUD inserter in accordance with a preferred embodiment of the present invention includes a generally elongate hollow shaft in the form of a tube 22 having a proximal end 24 and a distal end 26. The passageway extending through tube 22 between proximal end 24 and distal end 26 has a substantially uniform inner diameter of approximately 3.73 mm. A stop member such as flange 46 is adjustably mounted on tube 22 by a friction fit between the interior of flange 46 and the exterior surface of tube 22. Flange 46 has a rear end 48 which faces the proximal end 24 of tube 22, and a forward end 50 which faces the distal end 26 of the tube.

Figure 2:
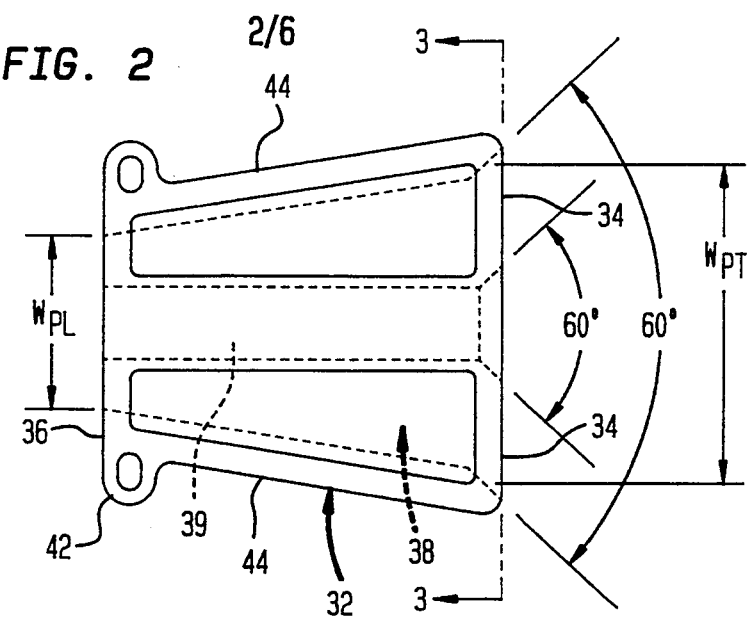
FIG. 2 is a diagrammatic plan view of a component used in the embodiment of FIG. 1.
Figure 3:
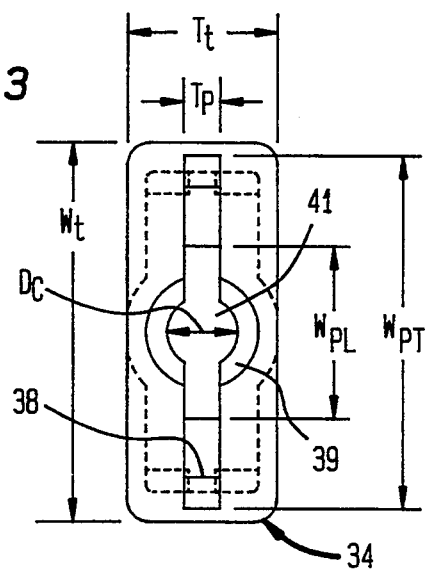
FIG. 3 is a diagrammatic elevational view taken along line 3—3 in FIG. 2.

An arm retainer generally designated 32 is also included in the IUD inserter. Arm retainer 32 is sized and shaped to be slidably mountable on elongate tube 22. Arm retainer 32 has a trailing edge 34 and a leading edge 36. As best seen in FIGS. 2 and 3, arm retainer 32 is generally in the form of a flat, substantially tapered parallelepiped. Trailing end 34 has a rectangular-shaped surface with a width $W_t$ of approximately 19.5 mm and a thickness $T_t$ of approximately 7.5 mm. Arm retainer 32 has a total length of approximately 20 mm from trailing edge 34 to leading edge 36. Tapered side walls 44 extend between trailing edge 34 and leading edge 36. A collar 42 protrudes outwardly from these tapered side walls at leading edge 36. The width and thickness dimensions of collar 42 at the leading edge are the same as those of the trailing edge surface.

Arm retainer 32 has a generally flat, slot-like passageway 38 extending between trailing end 34 and leading end 36. The major or widthwise dimension $W_{PT}$ of passageway 38 at trailing end 34 is approximately 15.4 mm. The passageway tapers down to a major or widthwise dimension $W_{PL}$ of approximately 8.7 mm where the passageway 38 intersects leading edge 36. The minor dimension or thickness $T_P$ of the slot-like passageway 38 is substantially constant at about 2.5 mm throughout the entire trailing end to leading end extent of the passageway. The passageway also has a pair of opposed, generally semicircular groove portions 39 cooperatively defining a generally cylindrical channel 41 intersecting slot-like channel 38 and extending from the trailing end 34 to the leading end 36. The interior diameter $D_c$ of the channel 41 desirably is about 4.5 mm, i.e., slightly larger than the exterior diameter of shaft 22.

The inserter, including elongate tube 22, flange 46 and arm retainer 32 can be manufactured from any material or compatible materials which are biologically safe. Most preferably, the elongate tube 22 can be made of high-density polyethylene such as Phillips' MARLEX EHM 6007 or PAXON AA60-007. Other preferable materials include polyethylene and polypropylene. Most preferably, the flange 46 is manufactured from polyvinyl chloride such as UNICHEM 7011-C2-02. Other preferable materials which can be used to make the flange 46 are polypropylene and polyethylene. The arm retainer 32 is preferably made of crystal polystyrene. However, other desirable materials include polycarbonate, acrylic, polypropylene, polyethylene, and polystyrene.

The IUD inserter may be used with an IUD such as the well-known "copper-tee" IUD. A "copper-tee" IUD (FIG. 1) has flexible arms 30a and 30b, respectively, and a body 30c located between arms 30a and 30b. These elements cooperatively define a generally T-shaped structure. In the position shown in FIG. 1, the IUD is arranged adjacent the distal end 26 of elongate tube 22 with the body 30 of the IUD extending proximally into the tube from distal end 26.

Figure 4:
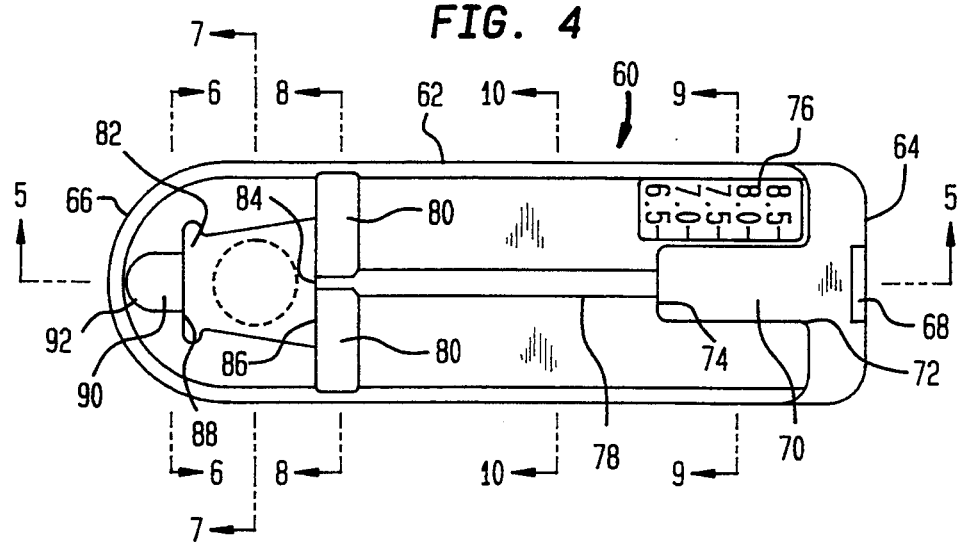
FIG. 4 is a top plan view of a further component used in the embodiment of FIG. 1.
Figure 5:
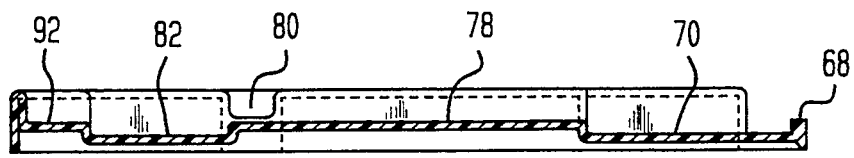
FIG. 5 is a sectional view taken along line 5—5 in FIG. 4.
Figure 6:
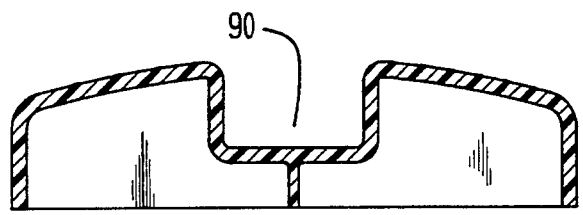
FIG. 6 is a sectional taken along line 6—6 in FIG. 4.
Figure 7:
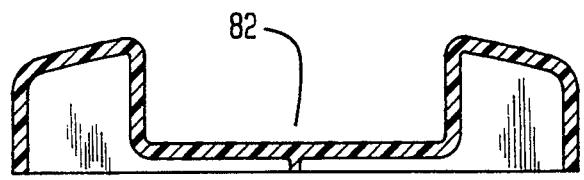
FIG. 7 is a sectional taken along line 7—7 in FIG. 4.
Figure 8:
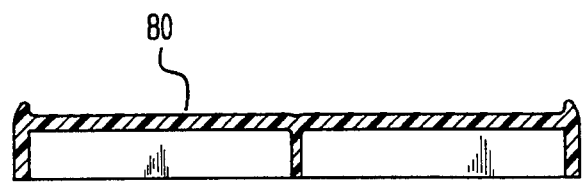
FIG. 8 is a sectional taken along line 8—8 in FIG. 4.
Figure 9:
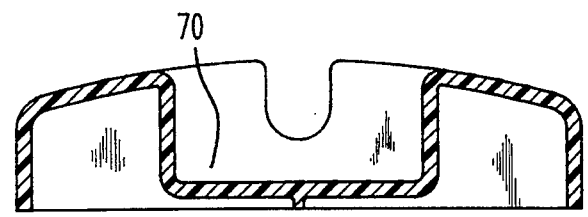
FIG. 9 is a sectional view taken along line 9—9 in FIG. 4.
Figure 10:
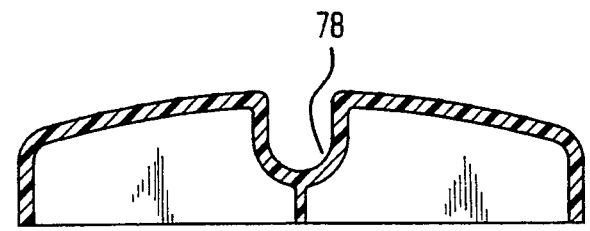
FIG. 10 is a sectional view taken along line 10—10 in FIG. 4.

The inserter and IUD are packaged in a tray 60. Tray 60 preferably includes a housing 62 having a proximal end 64 and a distal end 66. Most preferably, the tray 60 is made of crystal polystyrene, as is the arm retainer 32. Additional materials found to be suitable for the manufacture of tray 60 include polycarbonate, acrylonitrile, butadiene, styrene, polyethylene terephthalate, polyethylene terephthalate glycol, polyvinyl chloride, polypropylene, polyethylene and acrylic. As shown in FIG. 4, housing 62 comprises a continuous cavity including several compartments for retaining various portions of an IUD inserter such as inserter 20 described above, and an IUD such as the "copper-tee" also described above.

In particular, tray 60 includes a tube retainer 68 arranged adjacent proximal end 64 of housing 62 for securing a portion of an elongate tube such as tube 22 of inserter 20. A flange compartment 70 for retaining a flange, such as flange 46 of inserter 20, is formed adjacent tube retainer 68 on the distal side thereof. Flange compartment 70 is sized and shaped to retain flange 46 and to permit continuous unobstructed adjustment therein. Measurement indicia 76 are marked on the tray. These indicia begin at distal end 74 of flange compartment 70 and are increased in increments of 5.0 mm from distal end 74 toward proximal end 72 thereof.

A narrow elongate tube compartment 78 is sized and shaped to retain tube 22 of inserter 20 within housing 62 of tray 60. Tube compartment 78 extends distally from flange compartment 70. Further toward the distal end 66 of housing 62, the tray has a pair of arm compartments 80 and a groove portion 84 which extends between the arm compartments 80 so that the arm compartments 80 and elongate shaft compartment 78 are continuously connected in a T-shape.

An arm retainer compartment 82 has a proximal end 86 and a distal end 88. The arm retainer compartment is located on the distal side of compartments 80. As shown in FIG. 4, proximal end 86 of arm retainer compartment 82 is communicatably connected to expanded arm compartments 80 and groove 84. A pocket-like receptacle 90 is connected to distal end 88 of arm retainer compartment 82. Receptacle 90 has a vertically extending wall extending in an arc including the distal-most point 92 of the receptacle.

Most preferably, the entire housing of tray 62 and the compartments of the cavity therein are manufactured as a unitary body from one composition, and therefore, the individual compartments described above can be formed in a single mold to keep manufacturing costs at a minimum. Referring to the bottom surface of the tray 60 as a reference point of ground at 0.0 mm, the flange compartment 70 is preferably arranged approximately 2.0 mm from the ground reference. The arm retainer compartment 82 is preferably arranged approximately 2.5 mm from the ground reference and is thus arranged in a slightly higher plane than the flange compartment 70. It is desirable for the tube retainer 68 and the elongate tube compartment 22 to be raised a distance of approximately 1.9 mm above the horizontal plane of the arm retainer compartment and approximately 2.4 mm above the horizontal plane of the flange compartment. Tube retainer 68 and elongate tube compartment 78 should be relatively narrow so as to support elongate tube 22 as further discussed below.

The cavity defining copper-tee receptacle 90 is also raised a distance of approximately 2.5 mm above the horizontal plane of arm retainer cavity 82. In a preferred embodiment, the width of copper-tee receptacle 90 is approximately 9.5 mm in a widthwise direction transverse the proximal to distal direction of the tray.

In the preferred embodiment, the arm retainer compartment 82 is approximately 7.4 mm deep, 20 mm in length between proximal end 86 and distal end 88 thereof and has a width of approximately 20 mm at both proximal end 86 and distal end 88. Preferably, the expandable arm compartment 80 has a length of approximately 7.0 mm from the proximal to the distal end thereof, a width of approximately 34.00 mm and a depth of approximately 4.91 mm. Furthermore, it is desirable for the groove 84 to have a length of approximately 7.00 mm, a width of approximately 3.10 mm and a depth of approximately 5.51 mm. Moving further toward the proximal end of the tray 60, the elongate tube compartment 78 preferably has a length of approximately 46.00 mm, a width of approximately 4.7 mm, and a depth of approximately 5.51 mm. The flange compartment 80 is arranged proximately of the elongate tube compartment 78 and is about 25.00 mm in length, 13.5 mm in width, and 7.91 mm in depth. Additional sectional views of tray 60 are provided in FIGS. 6–10.

The tray 60, the IUD 30 and the inserter components such as tube 22, arm retainer 32 and flange 46 are prepackaged by the manufacturer in an envelope 61 (FIG. 1) which is adapted to maintain the packaged devices in a sterile condition. As packaged, and as stored prior to use, the tray holds the inserter components and IUD in the relative positions shown. Thus, the arms 30a and 30b of the IUD are disposed in arm compartments 80 of the tray, so that the arms remain in their normal or fully extended position during storage. As packaged and stored, the body 30c of the IUD extends proximally into tube 22 from the distal end thereof, so that the IUD as a whole is positioned at the distal end of the tube or shaft 22. The tray also holds the arm retainer 32 in position, within arm retainer cavity 82, so that the trailing end 34 of the arm retainer lies just distally of the IUD 30 and tube 22. In this as-packaged condition, the receptacle 90 of the tray is unoccupied. Flange 46 is disposed adjacent tube retainer 68 so that the proximal or rear end 48 of the flange abuts the tube retainer 68.

Figure 11:
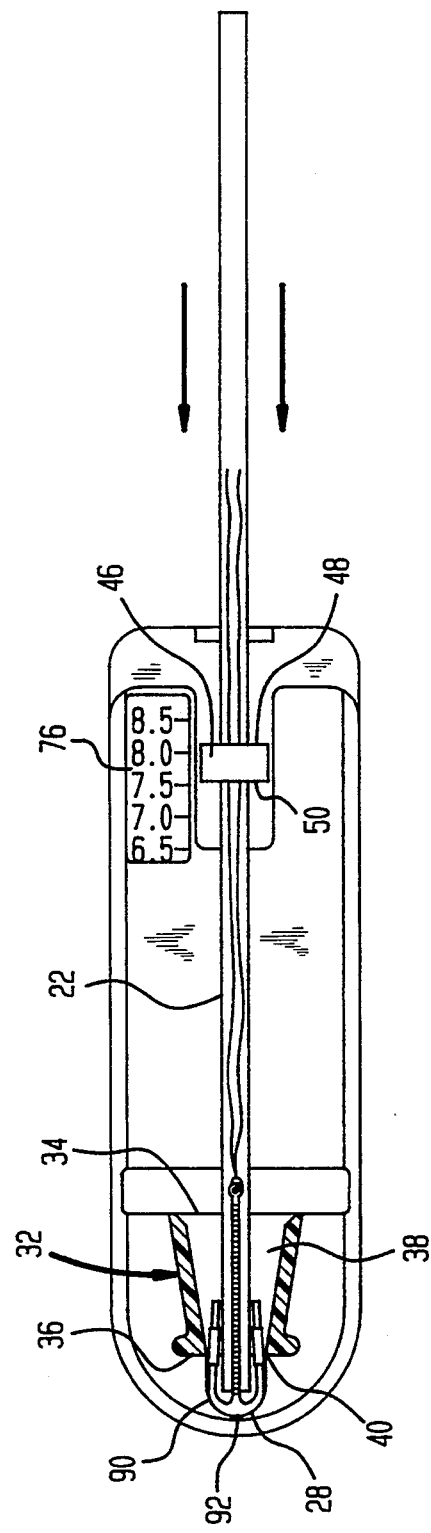
FIG. 11 is a diagrammatic, partially sectional view depicting certain elements shown in FIG. 1, but at a later stage of operation.

To "load" the IUD into the arm retainer by a method according to an embodiment of the invention, the user will open the envelope 60, grasp the proximal end 24 of tube 22 and then advance the tube distally toward arm retainer 32 within arm retainer cavity 82. Arms 30a and 30b of the IUD will then enter passageway 38 at trailing end 34 of the arm retainer. Tube 22 enters the cylindrical channel 41 (FIG. 3) of arm retainer 32, so that the tube and IUD body 30c are maintained in alignment with the trailing end and leading end axis of the arm retainer. The arm retainer has a "lead-in" or conical opening at the trailing end to facilitate entry of the tube. As best seen in FIG. 11, when distal end 26 of tube 22 is advanced toward copper-tee receptacle 90, arms 30a and 30b of the IUD become increasingly folded toward the sides of elongate tube 22 due to the tapered width of the passageway 38. The central portion 28 of the IUD arms 30a and 30b exit passageway 40 at leading end 36 of arm retainer 32. Distal end 26 is continuously advanced until the central portion 28 of the IUD arms 30a and 30b abut the distal-most portion 92 of receptacle 90. At this point, tube 22 can no longer be advanced toward distal end 66 of tray housing 62. In this condition, the outermost ends of arms 30a and 30b are retained by arm retainer 32.

After the tube and IUD have been fully advanced, and the distal end of the tube and IUD are at a fixed, predetermined location relative to the tray, flange 46 can be freely adjusted in either the proximal or the distal direction so that forward end 50 of the flange is aligned with a selected position relative to the tray based on indicia 76. The desired position corresponds to the uterus sounding measurement of a particular patient. For example, if a conventional uterus-sounding measurement for a particular patient indicates a uterine depth of 7.75 mm, the user will adjust flange 46 so that its forward end 50 lies midway between the "7.5" and "8.0" indicia on the tray. Once this has been done, the IUD inserter is fully loaded and adjusted and is ready for insertion into a particular patient having a uterine depth corresponding to the set location of flange 46.

The present method of loading the IUD into arm retainer 32 of IUD inserter 20, has many advantages over the prior art. In particular, the foregoing method enables a doctor to align forward end 50 of flange 46 precisely with the exact measurement corresponding to the uterine depth of a particular patient after arms 30a and 30b have been loaded into their folded position in arm retainer 32. There are no obstructions disposed within flange compartment 70 to reduce the accuracy through which flange 46 can be set. Furthermore, an important advantage of the present method is that the unit can be "loaded" while it remains within the confines of the tray. Indeed, the envelope 61 (FIG. 1) need only be opened partially to provide access to the proximal end of tube 22 and flange 46. It is not necessary to touch or expose the IUD itself, or the forward portions of tube 22, which will ultimately enter the uterus. This is a particularly important improvement over the prior art, such as the cartoned medical instrument package disclosed in the '633 patent to Roth, which required the IUD to be completely removed from the previously sterilized environment of the tray prior to being loaded in an inserter cap. Often, especially in poorer countries, the environment outside of the tray is unsanitary, thus making it entirely undesirable to load the IUD into an inserter device outside of the confines of its tray.

Moreover, the present method of loading an IUD into an inserter permits the unit to be precisely set to the measurements of a particular patient within the tray to assure that a patient is not injured during insertion of the IUD. The present method also permits the arms 30a and 30b of the copper-tee IUD to remain in their expanded state until immediately before inserting the IUD into a patient. This feature entirely removes the risk of the arms losing their elasticity due to the retention in a substantially folded position for an extended period of time.

At this time, the loaded unit is ready to be inserted into a patient in accordance with the preferred method for inserting an IUD according to a further aspect of the invention. As discussed above, in the loaded position, the IUD inserter, including elongate tube 22, adjustable flange 46 and slidably mounted arm retainer 32 are arranged so that an IUD is situated in its loaded position with arms 30a and 30b folded to extend substantially parallel with the outer wall of elongate tube 22. The central portion 28 of arms 30a and 30b, along with distal end 26 of elongate tube 22, extend a predetermined spaced distance beyond leading edge 36 of arm retainer 32. Most preferably, when the IUD is in its loaded position, distal end 26 of tube 22 will extend approximately 7 mm from leading edge 36 of arm retainer 32 and central portion 28 of arms 30a and 30b of the IUD will extend approximately 10 mm from the outermost portion of leading edge 36.

Figure 12:
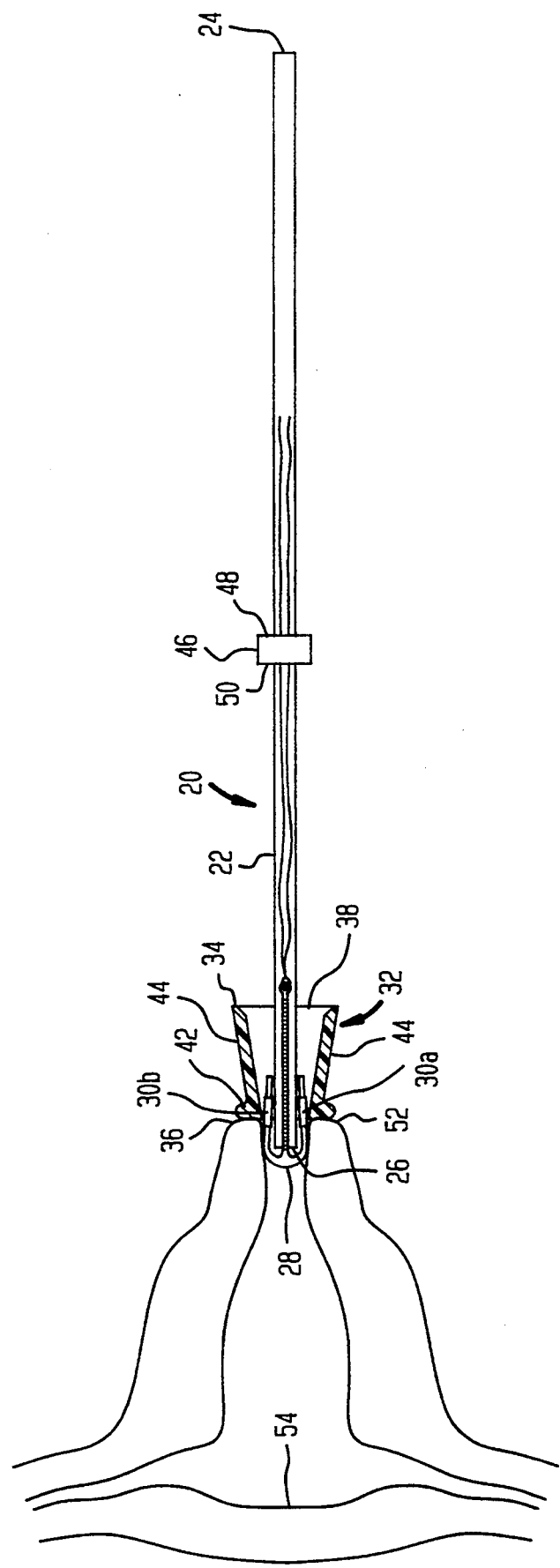
FIGS. 12 and 13 are further partially sectional views depicting certain elements shown in FIG. 11, but at still later stages of operation.

The loaded IUD inserter is removed from the tray and envelope and positioned as shown in FIG. 12. The leading edge 36 of slidable arm retainer 32 is placed against the outer portion 52 of a patient's cervix. It is desirable at this time to align the inserter and the loaded copper-tee therein with the cervical opening also as shown in FIG. 12. The protruding portions of the IUD 30 and tube distal end 26 aid in this alignment. As best shown in FIG. 3, the arm retainer 32 has a generally flat, slot-like passageway 38 which extends between the trailing end 34 and the leading end 36. As can be appreciated, the foregoing step of aligning the inserter and the loaded copper-tee IUD with the cervical opening of a patient, is greatly enhanced since the plane defined by the passageway 38 of the arm retainer 32 precisely indicates the plane of the arms 30a and 30b of the IUD immediately prior to insertion to the cervical os. Thus, the structure and operation of the arm retainer 32 provides a visual reference to the medical personnel inserting the IUD of the proper alignment position of the arms. Furthermore, the size and shape of the planar passageway 38 effectively prevents the arms of the IUD from spinning prior to or during insertion of same into a patient.

Figure 13:
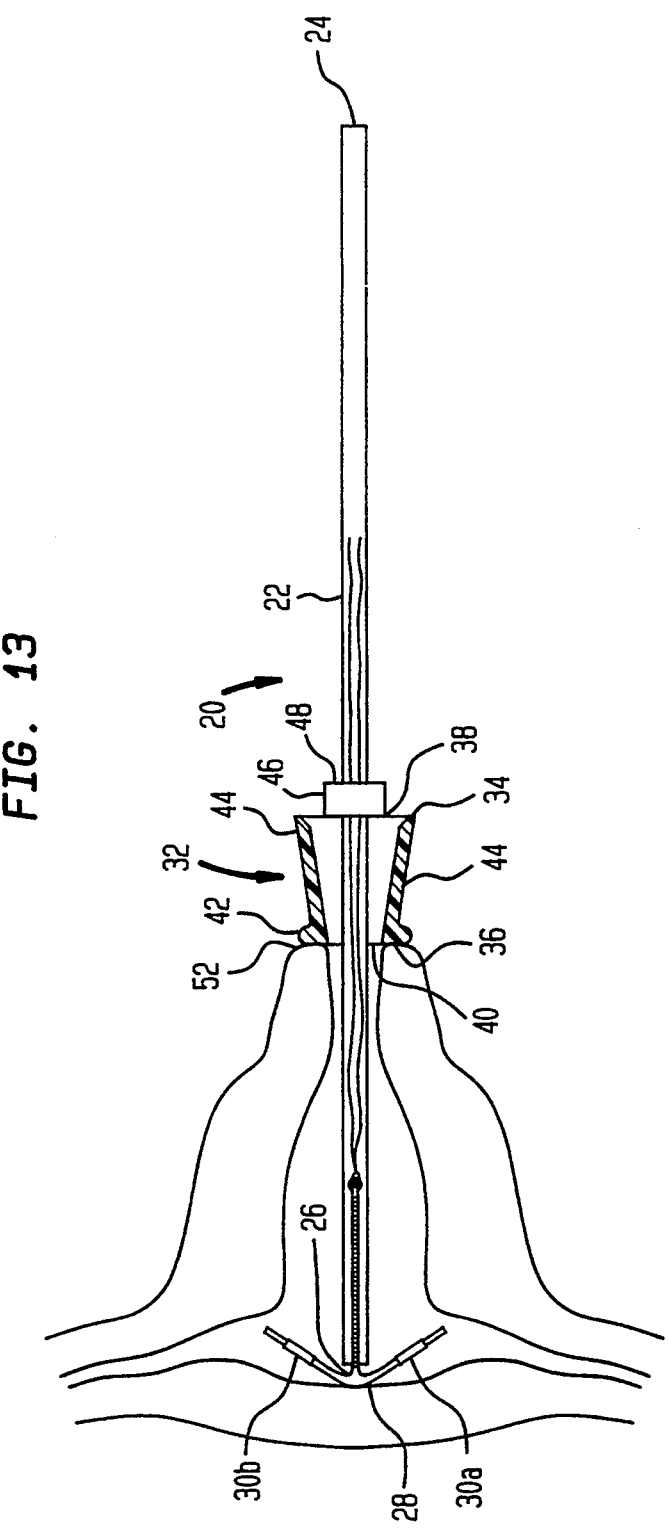

The user then grasps the elongate tube about proximal end 24 and advances the distal end 26 of tube 22 with the IUD thereon, through the cervical canal of a patient and into the uterus so that arms 30a and 30b of the IUD are permitted to return to their expanded position therein. At the same time, leading edge 36 of slidable arm retainer 32 remains in abutment with the outer portion of a patient's cervix 52. Thus, as the tube 22 advances, arm retainer 32 is forced proximally along the tube toward flange 46. As elongate tube 22 is advanced forward toward the uterine fundus 54, the outer portion of the cervix 52 continues to push arm retainer 32 proximally closer to forward end 50 of flange 46. This advancement process continues until trailing edge 34 of arm retainer 32 abuts forward end 50 of flange 46, as seen in FIG. 13. The abutting flange and arm retainer block further distal movement of tube 22. At this time, arms 30a and 30b are positioned in their expanded state against uterine fundus 54. Thus, the user who is inserting the IUD into the patient is provided with a failure-proof signal for preventing further advancement of distal end 26 of tube 22 and the IUD thereon into the uterine wall of the patient.

Finally, elongate tube 22 along with flange 46 and arm retainer 32 is withdrawn from the cervical opening, thereby leaving the "copper-tee" IUD with its arms 30a and 30b fully expanded at the uterine fundus of a patient.

The method and apparatus for inserting an IUD according to the present invention will permit a doctor or other qualified individual to safely insert a "copper-tee" IUD, or other IUD having expandable arms thereon, to the proper depth within the uterus of a patient without causing pain due to misalignment during insertion, and without causing trauma to the uterine wall of a patient, as may occur in prior art methods and apparatus when the IUD is accidentally advanced too far.

While the foregoing description and figures are directed toward the preferred method and apparatus in accordance with the present invention, it should be appreciated that numerous modifications can be made to each of the individual steps of the method and components of the entire apparatus as discussed above, and are indeed encouraged to be made in the steps, materials, structure and arrangement of the disclosed steps and embodiments of the present invention without departing from the spirit and scope of same. Thus, the foregoing description of the preferred steps and embodiments should be taken by way of illustration rather than by way of limitation with respect to the present invention as defined by the claims set forth below.

What is claimed is:

1. A method for loading expandable arms of an intrauterine device in an arm retainer of an intrauterine device inserter comprising the steps of, advancing an elongate shaft having a distal and a proximal end and having the intrauterine device positioned thereon with its arms initially in an expanded position so as to advance the expandable arms of the intrauterine device and the distal end of the elongate shaft inside an arm retainer so that the arms of the intrauterine device are forced from their expanded position to a substantially folded position, said advancing step being performed while said intrauterine device and said arm retainer remain in a package so that loading of the expandable arms of said arm retainer is facilitated.

2. The method of claim 1, wherein the step of advancing the elongate shaft comprises the step of arresting the advancing movement of the shaft and the intrauterine device by engaging at least one of the shaft and the intrauterine device with an abutment surface on the package.

3. The method of claim 2, further comprising the step of adjusting a stop member having a forward edge and a rear edge on the elongate shaft so that the forward edge of the stop member is aligned with measurement indicia on a tray which corresponds to the proper uterine depth of a patient.

4. An inserter for an intrauterine device having expandable arms thereon comprising, an elongate shaft having a proximal and a distal end, said shaft being adapted to retain an intrauterine device adjacent said distal end;

a leading member slidably mounted on said elongate shaft adjacent said distal end thereof, said leading member having a leading end and a trailing end; and a stop member mounted on said elongate shaft for adjustment within a range of proximal-to-distal positions proximal to said leading member, said stop member having a rear end and a forward end and being disposed whereby the forward end of said stop member abuts the trailing end of said leading member when said distal end of said shaft is advanced through the cervical canal of a patient into the uterus to a preselected depth while said leading end of said leading member abuts the outer portion of the cervix.

5. The inserter of claim 4, wherein said leading member is an arm retainer, said arm retainer comprises a body, said body being hollow so as to define a passageway therethrough from said trailing end to said leading end, said passageway having a preselected interior dimension at said leading end of said arm retainer so that the expandable arms of the intrauterine device will be retained in a substantially folded position when said intrauterine device is positioned in said passageway of said arm retainer.

6. The inserter of claim 5, wherein said interior dimension of said passageway through said arm retainer is narrower at said leading end than it is at said trailing end.

7. The inserter of claim 6, wherein said passageway has a generally rectangular cross-sectional shape having orthogonal major and minor dimensions, said preselected interior dimension being the major dimension of said rectangular cross-section shape.

8. The inserter of claim 7, wherein said minor dimension of said generally rectangular cross-sectional shape is substantially constant from said trailing end to said leading end.

9. The inserter of claim 7, wherein said passageway includes a groove section extending from said trailing end of said arm retainer to said leading end thereof, said minor dimension of said passageway being greater in said groove section than in immediately adjacent regions of said passageway, said shaft being engageable in said groove section.

10. The inserter of claim 9, wherein said arm retainer comprises a collar formed about said leading end, said collar being arranged to abut the outer portion of a patient's cervix during insertion of said intrauterine device into the uterus of a patient.

11. An inserter for an intrauterine device having expandable arms thereon comprising, an elongate shaft having a proximal and a distal end, said shaft being adapted to retain the intrauterine device adjacent said distal end; and a leading member slidably mounted on said elongate shaft adjacent said distal end thereof, said leading member having a leading end and a trailing end, said leading member being an arm retainer, said arm retainer comprises a body, said body being hollow so as to define a passageway therethrough from said trailing end to said leading end, said passageway having a preselected interior dimension which is greater at said trailing end than said leading end of said arm retainer, said interior dimension of said passageway converging from a relatively large dimension to a relatively small dimension between said trailing end and said leading end so that the expandable arms of the intrauterine device will be placed into a substantially folded position upon advancement through said passageway.

12. The inserter of claim 11 further comprising a stop member mounted on said elongate shaft for adjustment within a range of proximal-to-distal positions proximal to said leading member, said stop member having a rear and forward end and being disposed whereby the forward end of said stop member abuts the trailing end of said leading member when said distal end of said shaft is advanced through the cervical canal of a patient into the uterus to a preselected depth while said leading end of said leading member abuts the outer portion of the cervix.

13. The inserter of claim 12, wherein said arm retainer comprises a collar formed about said leading end, said collar being arranged to abut the outer portion of a patient's cervix during insertion of said intrauterine device into the uterus of a patient.

14. An inserter for a intrauterine device having expandable arms thereon comprising, an elongate shaft having a proximal end and a distal end, said shaft being adapted to retain an intrauterine device adjacent said distal end; a leading member slidably mounted on said elongated shaft adjacent said distal end thereof, said leading member having a leading end and a trailing end, said leading member being an arm retainer, said arm retainer comprises a body, said body being hollow so as to define a passageway thereto from said trailing end to said leading end, said passageway having a preselected sized and shaped opening at the leading end of said arm retainer arranged to prevent misalignment such as twisting of said expandable arms of said IUD prior to insertion through the cervical canal of a patient.

15. The inserter of claim 14 further comprising a stop member mounted on said elongate shaft for adjustment within a range of proximal-to-distal positions proximal to said leading member, said stop member having a rear end and a forward end and being disposed whereby the forward end of said stop member abuts the trailing end of said leading member when said distal end of said shaft is advanced through the cervical canal of a patient into the uterus to a preselected depth while said leading end of said leading member abuts the outer portion of the cervix.

16. The inserter of claim 15 wherein said passageway through said body of said arm retainer has a greater dimension at said trailing end than at said leading end thereof.

17. The inserter of claim 16, wherein said arm retainer comprises a collar formed about said leading end, said collar being arranged to abut the outer portion of a patient's cervix during insertion of said intrauterine device into the uterus of a patient.

* * * * *